US009737315B2

(12) United States Patent
Birmingham (10) Patent No.: US 9,737,315 B2
(45) Date of Patent: Aug. 22, 2017

(54) METHOD AND DEVICE FOR JOINT REPLACEMENT

(71) Applicant: Zimmer, Inc., Warsaw, IN (US)

(72) Inventor: Patrick M. Birmingham, Glencoe, IL (US)

(73) Assignee: Zimmer, Inc., Warsaw, IN (US)

( * ) Notice: Subject to any disclaimer, the term of this patent is extended or adjusted under 35 U.S.C. 154(b) by 55 days.

(21) Appl. No.: 14/559,260

(22) Filed: Dec. 3, 2014

(65) Prior Publication Data

US 2015/0094727 A1 Apr. 2, 2015

Related U.S. Application Data

(62) Division of application No. 13/943,862, filed on Jul. 17, 2013.

(60) Provisional application No. 61/676,041, filed on Jul. 26, 2012.

(51) Int. Cl.
*A61F 2/36* (2006.01)
*A61B 17/16* (2006.01)
*A61F 2/32* (2006.01)
*A61B 17/17* (2006.01)
*A61F 2/30* (2006.01)
*A61F 2/46* (2006.01)

(52) U.S. Cl.
CPC ...... *A61B 17/1664* (2013.01); *A61B 17/1666* (2013.01); *A61B 17/175* (2013.01); *A61F 2/32* (2013.01); *A61F 2/3603* (2013.01); *A61F 2002/30754* (2013.01); *A61F 2002/3208* (2013.01); *A61F 2002/4635* (2013.01)

(58) Field of Classification Search
CPC ............... A61F 2002/30754; A61F 2/3603
See application file for complete search history.

(56) References Cited

U.S. PATENT DOCUMENTS

| 4,678,472 A | 7/1987 | Noiles |
| 4,950,299 A | 8/1990 | Noiles |
| 4,976,740 A * | 12/1990 | Kleiner ............ A61B 17/1668 623/23.14 |

(Continued)

FOREIGN PATENT DOCUMENTS

| DE | 10338420 A1 | 3/2005 |
| DE | 102008053566 A1 | 6/2009 |

(Continued)

OTHER PUBLICATIONS

International Search Report and Written Opinion for international application No. PCT/US2013/051611, mailing date Nov. 8, 2013, 7 pages.

(Continued)

*Primary Examiner* — David Bates
(74) *Attorney, Agent, or Firm* — Schwegman Lundberg & Woessner, P.A.

(57) ABSTRACT

A method of joint replacement including forming one or more arthroscopy portals adjacent a hip joint that includes, a femur with a femoral head and a pelvis with an acetabulum socket, inserting a hemiarthroplasty cup, having a cup inner surface and a cup outer surface, between a femoral head outer surface of the femoral head and an acetabulum outer surface of the acetabulum socket, wherein at least one of the femoral head outer surface and the acetabulum other surface are unreamed.

13 Claims, 5 Drawing Sheets

(56) References Cited

U.S. PATENT DOCUMENTS

| | | | |
|---|---|---|---|
| 5,004,476 A | 4/1991 | Cook | |
| 5,571,191 A * | 11/1996 | Fitz | A61F 2/4405 606/247 |
| 5,725,593 A * | 3/1998 | Caracciolo | A61F 2/32 623/22.23 |
| 5,800,553 A * | 9/1998 | Albrektsson | A61B 17/1668 606/65 |
| 5,997,582 A | 12/1999 | Weiss | |
| 6,383,227 B1 * | 5/2002 | Baroud | A61F 2/3601 623/23.11 |
| 6,482,237 B2 * | 11/2002 | Mosseri | A61B 17/1666 623/22.12 |
| 6,695,883 B2 * | 2/2004 | Crofford | A61B 17/175 623/22.46 |
| 7,393,362 B2 | 7/2008 | Cruchet et al. | |
| 8,632,601 B2 * | 1/2014 | Howald | A61F 2/4603 623/22.11 |
| 8,663,293 B2 * | 3/2014 | Assell | A61F 2/4405 606/279 |
| 8,961,613 B2 * | 2/2015 | Assell | A61F 2/3872 606/60 |
| 8,979,935 B2 | 3/2015 | Lozier et al. | |
| 9,039,780 B2 * | 5/2015 | Forsell | A61B 17/1617 623/23.14 |
| 9,060,789 B2 * | 6/2015 | Weinstein | A61B 17/1682 |
| 2003/0130741 A1 | 7/2003 | McMinn | |
| 2004/0199166 A1 * | 10/2004 | Schmieding | A61B 17/1617 606/79 |
| 2006/0085080 A1 | 4/2006 | Bechgaard et al. | |
| 2006/0235539 A1 * | 10/2006 | Blunn | A61B 17/1666 623/22.12 |
| 2008/0033577 A1 | 2/2008 | Kohan | |
| 2008/0208347 A1 | 8/2008 | Muratoglu et al. | |
| 2008/0262626 A1 | 10/2008 | Raugel | |
| 2009/0005879 A1 | 1/2009 | Tuke et al. | |
| 2009/0018666 A1 | 1/2009 | Grundei et al. | |
| 2009/0048681 A1 | 2/2009 | Vlachos | |
| 2009/0088846 A1 * | 4/2009 | Myung | A61F 2/30756 623/14.12 |
| 2009/0234459 A1 | 9/2009 | Sporring et al. | |
| 2009/0281545 A1 * | 11/2009 | Stubbs | A61B 17/1666 606/87 |
| 2011/0152868 A1 * | 6/2011 | Kourtis | A61B 17/025 606/80 |
| 2011/0196378 A1 * | 8/2011 | Flom | A61B 17/025 606/90 |
| 2011/0301654 A1 | 12/2011 | Wozencroft et al. | |
| 2012/0116531 A1 * | 5/2012 | Forsell | A61F 2/3603 623/23.11 |
| 2012/0130502 A1 | 5/2012 | Podolsky et al. | |
| 2013/0018479 A1 | 1/2013 | Grotz et al. | |
| 2014/0031948 A1 | 1/2014 | Birmingham | |
| 2015/0045909 A1 | 2/2015 | Muratoglu et al. | |
| 2015/0134072 A1 | 5/2015 | Forsell | |

FOREIGN PATENT DOCUMENTS

| | | |
|---|---|---|
| EP | 0728449 A2 | 8/1996 |
| FR | 2297030 A1 | 8/1976 |
| GB | 2007980 | 5/1979 |

OTHER PUBLICATIONS

U.S. Non-Final Office action for U.S. Appl. No. 13/943,862, dated Dec. 11, 2014, 8 pages.

"U.S. Appl. No. 13/943,862, Final Office Action mailed Apr. 8, 2016", 12 pgs.

"U.S. Appl. No. 13/943,862, Final Office Action mailed Jul. 14, 2015", 9 pgs.

"U.S. Appl. No. 13/943,862, Non Final Office Action mailed Nov. 25, 2015", 13 pgs.

"U.S. Appl. No. 13/943,862, Response filed Feb. 25, 2016 to Non Final Office Action mailed Nov. 25, 2015", 11 pgs.

"U.S. Appl. No. 13/943,862, Response filed Jun. 2, 2015 to Non Final Office Action mailed Dec. 11, 2014", 12 pgs.

"U.S. Appl. No. 13/943,862, Response filed Nov. 16, 2015 to Final Office Action mailed Jul. 14, 2015", 11 pgs.

"U.S. Appl. No. 13/943,862, Response filed Dec. 3, 2014 to Restriction Requirement mailed Oct. 14, 2014", 8 pgs.

"U.S. Appl. No. 13/943,862, Restriction Requirement mailed Oct. 14, 2014", 7 pgs.

"European Application Serial No. 13823085.9, Extended European Search Report mailed Mar. 1, 2016", 7 pgs.

"European Application Serial No. 13823085.9, Response filed Oct. 12, 2015 to Communication pursuant to Rules 161(2) and 162 EPC mailed Mar. 31, 2015", 8 pgs.

"International Application Serial No. PCT/US2013/051611, International Preliminary Report on Patentability mailed Feb. 5, 2015", 7 pgs.

"Australian Application Serial No. 2013293195, First Examiner Report dated Jan. 27, 2017", 5 pgs.

"Australian Application Serial No. 2013293195, Response dated May 5, 2017 to First Examiner Report dated Jan. 27, 2017", 19 pgs.

"European Application Serial No. 13823085.9, European Office Action dated Apr. 24, 2017", 6 pgs.

* cited by examiner

METHOD AND DEVICE FOR JOINT REPLACEMENT

CROSS REFERENCE TO RELATED APPLICATION

This application claims the benefit of U.S. patent application Ser. No. 13/943,862 filed on Jul. 17, 2013 entitled "Method and Device for Joint Replacement," and U.S. Provisional Patent Application No. 61/676,041 filed on Jul. 26, 2012 entitled "Method and Device for Joint Replacement," both of which are hereby incorporated herein by reference, in their entirety.

RELATED FIELD

The method and device for joint replacement relates to joint repair and replacement.

BACKGROUND

Joints provide articulation of various body parts. These joints can be damaged in numerous ways, such as exposure to trauma or degeneration due to old age or disease. Joints, such as hip joints, typically include a bone with a ball end and a bone with a socket opening. When damaged, the interaction between the ball and socket can become problematic, preventing proper articulation of a joint and/or pain in the joint. Such restriction and/or discomfort are often due to a breakdown of the surfaces of one or both of the ball and socket. In the case of a hip joint, the femur and pelvis are involved. The femur includes the femoral head with a layer of articular cartilage and the pelvic bone includes the acetabulum socket, also with a layer of articular cartilage. Once the layer of articular cartilage is worn or damaged to an advanced degree, the joint no longer functions as intended and can require surgical intervention.

Currently, to address worn or damaged hip joints, an invasive surgical procedure is performed to install a full or half prosthetic joint. The installation of the prosthetic joint involves substantial restructuring of the original joint, which requires the surgeon to inflict substantial damage to the joint area to access and install the prosthetic joint, thereby increasing the likelihood of permanent damage to surrounding nerves, ligaments, etc. In addition, this invasive procedure can result in chronic pain, poor articulation of the joint, failure of the prosthesis, etc., which can substantially decrease the likelihood of a postoperative normally functioning prosthetic joint.

Accordingly, it would be desirable to provide a minimally invasive procedure that limits the damage to the joint area during installation and provide a more reliable prosthetic repair/replacement.

BRIEF SUMMARY

In at least some embodiments, the method of joint replacement relates to forming one or more arthroscopy portals adjacent a hip joint that includes a femur and a pelvis; inserting a guide wire through a portion of the femur to extend out of a femoral head of the femur; securing a reamer blade to the guide wire; reaming a femoral head outer surface at the end of the femoral head to at least one of access cancellous bone and remove damaged cartilage; reaming an acetabulum outer surface of the acetabulum socket of the pelvis to at least one of access cancellous bone and remove damaged cartilage; unsecuring the reamer blade from the guide wire; and inserting a hemiarthroplasty cup between the femoral head outer surface and the acetabulum outer surface.

In at least some embodiments, the method of joint replacement relates to forming one or more arthroscopy portals adjacent a hip joint that includes a femur and a pelvis; inserting a guide wire through a portion of the femur to extend out of a femoral head of the femur; securing a reamer blade to the guide wire; reaming a femoral head outer surface at the end of the femoral head to at least one of access cancellous bone and remove damaged cartilage; reaming an acetabulum outer surface of the acetabulum socket of the pelvis to at least one of access cancellous bone and remove damaged cartilage; unsecuring the reamer blade from the guide wire; rotating a cannulated drill around the guide wire and through the femur; inserting a cannulated fastener in place of the cannulated drill; inserting a cup femoral head prosthesis adjacent to the femoral head outer surface; securing the cup femoral head prosthesis to the femoral head outer surface using the cannulated fastener; and inserting a hemiarthroplasty cup between the femoral head outer surface and the acetabulum outer surface.

In at least some embodiments, the method of joint replacement relates to forming one or more arthroscopy portals adjacent a hip joint that includes a femur and a pelvis; inserting a guide wire through a portion of the femur to extend out of a femoral head of the femur; securing a reamer blade to the guide wire; reaming a femoral head outer surface at the end of the femoral head to at least one of access cancellous bone and remove damaged cartilage; reaming an acetabulum outer surface of the acetabulum socket of the pelvis to at least one of access cancellous bone and remove damaged cartilage; unsecuring the reamer blade from the guide wire; rotating a cannulated drill around the guide wire and through the femur; inserting a cannulated fastener in place of the cannulated drill; inserting a cup femoral head prosthesis adjacent to the femoral head outer surface; and securing the cup femoral head prosthesis to the femoral head outer surface using the cannulated fastener.

In at least some embodiments, a device for joint replacement relates to a prosthesis including a hemiarthroplasty cup including an inner surface and an outer surface, wherein the inner surface is shaped and sized to accommodate a reamed or unreamed femoral head outer surface, and wherein the outer surface is shaped and sized to accommodate a reamed or unreamed acetabulum outer surface of an acetabulum socket.

In at least some embodiments, a device for joint replacement relates to a prosthesis including an at least partially hemispherical-shaped cup including an inner surface and an outer surface, wherein the inner surface is shaped and sized to accommodate a reamed femoral head outer surface of a femur, and wherein the outer surface is shaped and sized to accommodate at least one of a reamed or unreamed acetabulum outer surface of an acetabulum socket and an inner surface of a hemiarthroplasty cup; a fastener securable to the femur for engagement with a portion of the hemispherical-shaped cup to provide securement of the hemispherical-shaped cup to the femoral head outer surface.

In at least some embodiments, a device for joint replacement relates to a prosthesis including a hemiarthroplasty cup including an inner surface shaped and sized to accommodate a reamed or unreamed femoral head outer surface, and an outer surface shaped and sized to accommodate a reamed or unreamed acetabulum outer surface of an acetabulum socket, wherein the hemiarthroplasty cup is configured to maintain allowance of articulation of the femoral head outer surface and the acetabulum socket relative to the hemiarthroplasty cup after implantation.

In at least some embodiments, a device for joint replacement relates to a prosthesis including an at least partially hemispherical-shaped cup including an inner surface and an outer surface, wherein the inner surface is shaped and sized to accommodate at least one of a reamed femoral head outer surface of a femur and a cup femoral head prosthesis, and wherein the outer surface is shaped and sized to accommodate a reamed acetabulum outer surface of an acetabulum socket.

In at least some embodiments, a device for joint replacement relates to a prosthesis including a cup-shaped portion including an inner surface and an outer surface, wherein the inner surface is shaped and sized to accommodate at least one of a reamed femoral head outer surface of a femur and a cup femoral head prosthesis, and wherein the outer surface is shaped and sized to accommodate a reamed or unreamed acetabulum outer surface of an acetabulum socket.

Other embodiments, aspects, features, objectives, and advantages will be understood and appreciated upon a full reading of the detailed description and the claims that follow.

BRIEF DESCRIPTION OF THE DRAWINGS

Embodiments of the method and device for joint replacement are disclosed with reference to the accompanying drawings and are for illustrative purposes only. The method and device for joint replacement is not limited in its application to the details of construction or the arrangement of the components illustrated in the drawings. The method and device for joint replacement is capable of other embodiments or of being practiced or carried out in other various ways. In the drawings.

DETAILED DESCRIPTION

Figure 1:
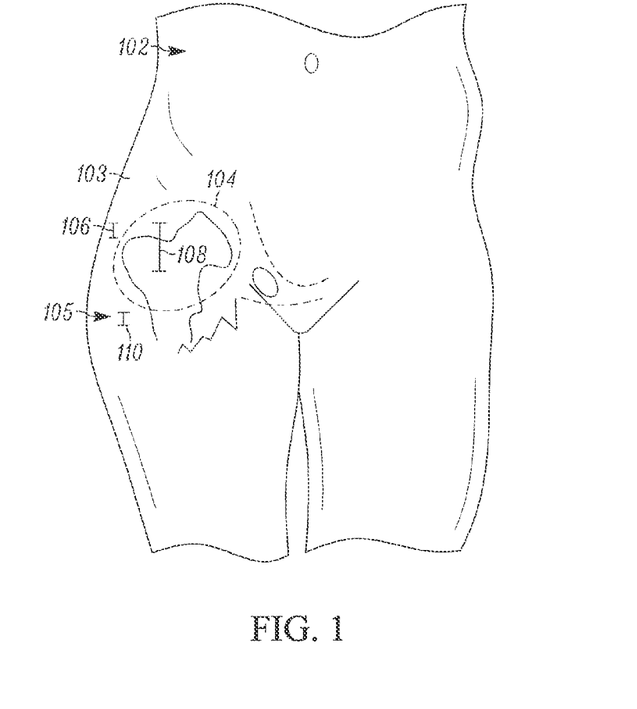
FIG. 1 illustrates a front view of a portion of an example of a human body with an example of a hip joint.

Referring to FIG. 1, a front view of a portion of an example of a human body 102 is illustrated. The body 102 is shown with a plurality of hip arthroscopy portals 105 identified. These hip arthroscopy portals 105 are provided to allow access past skin 103, muscle, ligaments, etc., to the hip joint 104 and are established as needed during a hip repair/replacement procedure. The arthroscopy portals illustrated include an anterolateral portal 106, a midanterior portal 108, and a distal anterolateral portal 110, although one or more of various other types of arthroscopy portals can be provided in place of or in addition to these portals.

Figure 2:
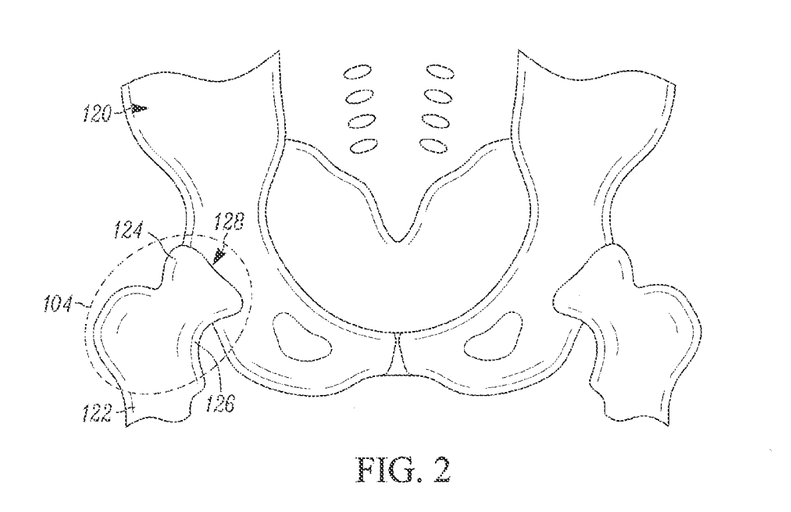
FIG. 2 illustrates an example of a front skeletal view of the hip joint of FIG. 1.
Figure 3:
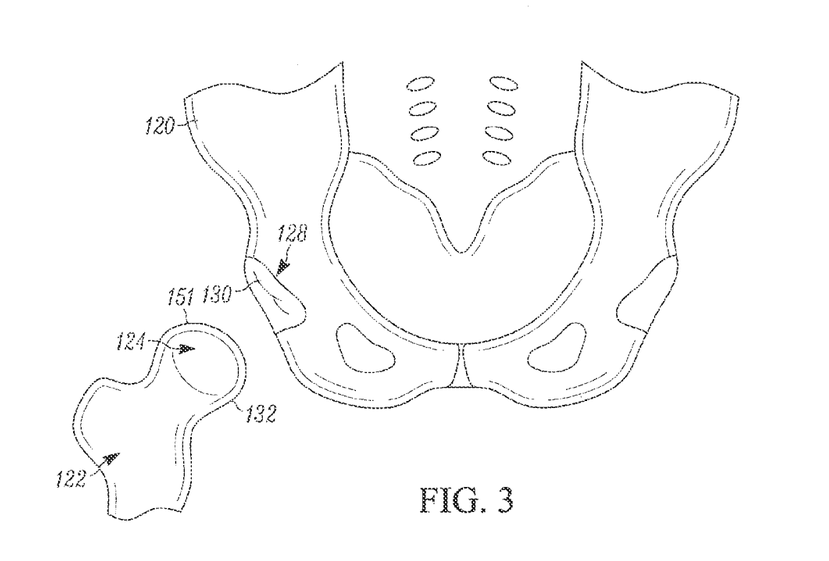
FIG. 3 illustrates a view of FIG. 2 with the femur distracted from the pelvis.

Referring to FIG. 2, a front skeletal view of the hip joint 104 is provided. The hip joint 104 includes at least portions of a pelvis 120 and a femur 122. The femur 122 includes a femoral head 124 connected to the femur 122 by a femoral neck 126. The pelvis 120 includes an acetabulum socket 128, which is a socket formed in the pelvis 120. In FIG. 2, the femoral head 124 is shown in its natural seated position in the acetabulum socket 128. FIG. 3 illustrates a view of the hip joint 104 of FIG. 2 with the femur 122 distracted from the pelvis 120. The distraction exposes an acetabulum outer surface 130 and a femoral head outer surface 132. The acetabulum outer surface 130 and femoral head outer surface 132 are at least partially comprised of a layer of articular cartilage 141 (FIG. 4).

As a result of trauma, disease, and/or degeneration, the articular cartilage 141 can become damaged resulting in a rough or irregular surface. In some cases, at least portions of the articular cartilage 141 can be substantially worn away. These conditions reduce or eliminate the normally smooth engagement of the femoral head 124 and the acetabulum socket 128. In order to provide the smooth surfaces desired for proper joint function, one or both of the acetabulum outer surface 130 and femoral head outer surface 132 are at least one of, resurfaced for engaging with a prosthesis or at least partially covered with a prosthesis. This can be achieved through at least the use of the procedures and prosthesis as described below.

Figures 4, 5, 6, 7:
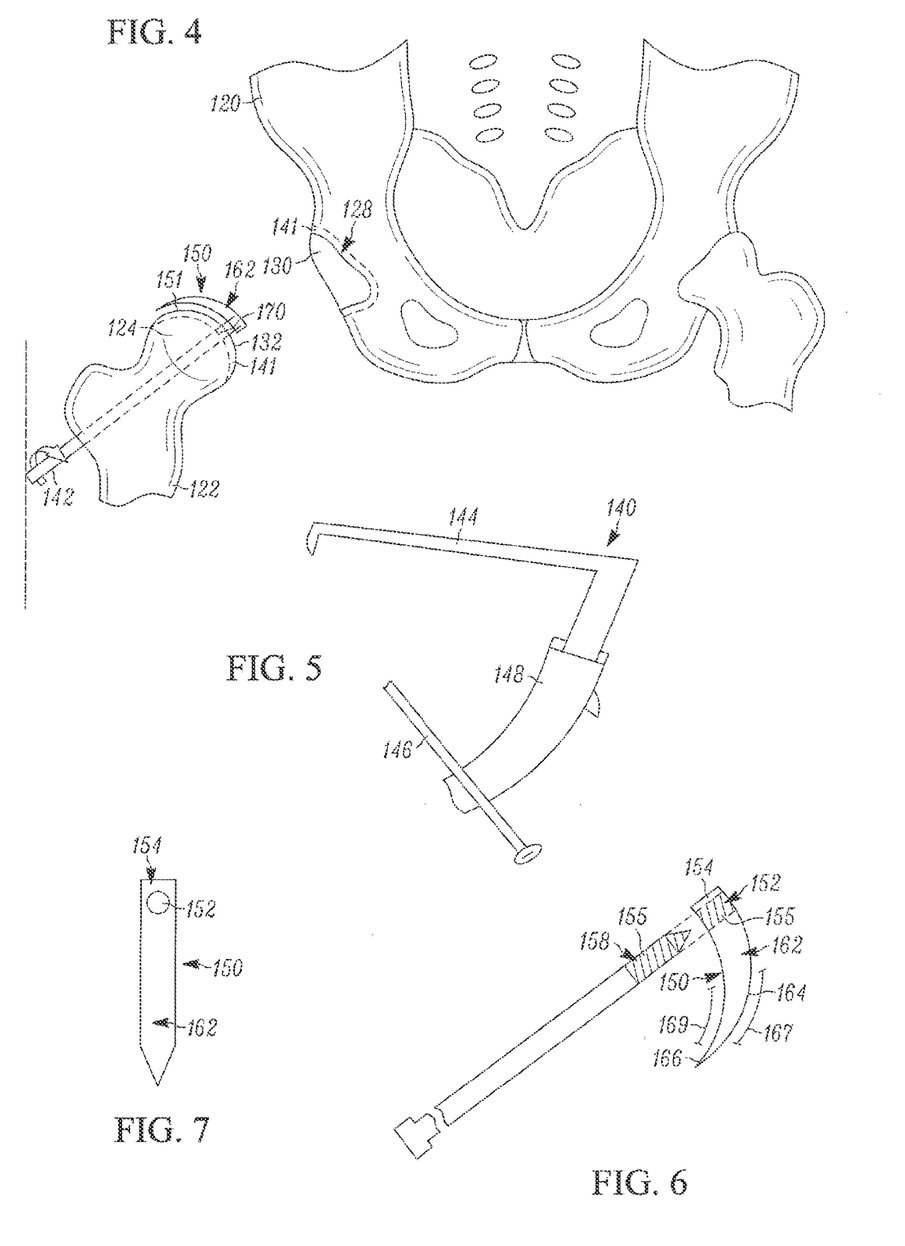
FIG. 4 illustrates another view of the femur and pelvis of FIG. 3.
FIG. 5 illustrates an example of a drill guide.
FIG. 6 illustrates an example of a guide wire and an example of a reamer.
FIG. 7 illustrates a top view of the reamer of FIG. 6.

Referring now to FIG. 4, another view of the hip joint 104 of FIG. 3 is illustrated. It is not evident by the illustrations, but it is to be understood that one or both of the acetabulum socket 128 and femoral head 124 can be damaged or otherwise in need of repair or replacement. The procedure described below can include the use of one or more of various tools as described below. FIG. 5 illustrates a drill guide 140 utilized for inserting a guide wire 142 (FIG. 4) into the femur 122. The drill guide 140 includes an aiming arm 144 and a drill sleeve 146, both interconnected by a handle 148. In addition, referring to FIGS. 6 and 7, a reamer 150 is provided for resurfacing an end 151 of the femoral head outer surface 132 and/or acetabulum outer surface 130. The reamer 150 is shown as sickle-shaped, although it is contemplated that the shape and size of the reamer 150 can be modified as needed to accommodate various bone and prosthesis shapes and sizes. A fastening portion, such as a locking aperture 152 can be provided at a base portion 154 of the reamer 150. The locking aperture 152 is configured to be securable to the guide wire 142. The securement can be accomplished by one or more of various methods, such as providing reverse threads 155 in the locking aperture 152 for rotational engagement with reverse threads 155 on a guide wire end portion 158. In addition, the reamer 150 includes an engagement portion 162 having a top edge 164 and bottom edge 166. The top edge 164 includes a radius of curvature 167 shaped to conform to a desired shape for the acetabulum outer surface 130. The bottom edge 166 includes a radius of curvature 167 shaped to conform to a desired shape for the end 151 of the femoral head outer surface 132. Further, the engagement portion 162 can be tapered as it extends away from the base portion 154. In at least some embodiments, the top edge 164 and bottom edge 166 each comprise a bladed edge, although other shapes and configurations can be utilized to provide the desired resurfacing effect.

In at least some embodiments, to begin a hip joint repair or replacement procedure, a patient is positioned on a hip arthroscopy traction table, in a supine, lateral, or other position as desired. The hip is distracted, as illustrated in FIG. 4, to provide the necessary access to the femur 122 and acetabulum socket 128. The hip arthroscopy portals 105 are formed as necessary, as shown in FIG. 1. Upon entry into the body 102, the hip ligamentous capsule (not shown) is cut to provide the necessary access, for example from a 10 o'clock to 2 o'clock position. The drill guide 140 is then placed through the distal anterolateral portal 110 or others as desired, and the drill sleeve 146 is pushed to the skin 103. After a small incision is made, the guide wire 142 is advanced through the femur 122 by a drill (not shown) to its aimed location (determined by the positioning of the aiming arm 144 and drill sleeve 146), which is the center 170 of the femoral head 124. After installation of the guide wire 142, the drill guide 140 is removed and the midanterior portal 108 is enlarged to provide greater access, such as to a diameter of about 4 centimeters, or other necessary size. The guide wire 142 is now positioned to receive the reamer 150. The reamer 150 is inserted through the midanterior portal 108 and positioned so the reverse threads 155 of the guide wire 142 rotationally engage the reverse threads 155 of the locking aperture 152 to allow the reamer 150 to be locked to the guide wire 142.

The drill is secured to the guide wire 142 and energized to rotate the guide wire 142. As the guide wire 142 rotates, the secured reamer 150 also rotates. Placing a pulling tension on the guide wire 142, such that the bottom edge 166 of the rotating reamer 150 engages the end 151 of the femoral head outer surface 132, serves to ream down the end 151 of the femoral head outer surface 132 at least partially to cancellous bone and/or to remove damaged cartilage, thereby partially, substantially, or completely removing the articular cartilage layer from the femoral head 124. The radius of curvature 167 along the bottom edge 166 of the engagement portion 162 can be chosen to form the end 151 of the femoral head outer surface 132 to a desired shape, such as a symmetrical hemispherical shape. Similarly, advancing (pushing tension) the guide wire 142 during rotation, such that the top edge 164 of the rotating reamer 150 engages the acetabulum outer surface 130, serves to ream down the acetabulum outer surface 130 at least partially to cancellous bone and/or to remove damaged cartilage, thereby partially, substantially, or completely removing the articular cartilage layer from the acetabulum socket 128. The radius of curvature 167 along the top edge 164 of the engagement portion 162 can be chosen to form the acetabulum outer surface 130 to a desired shape, such as a symmetrical hemispherical shape. Upon completion of the reaming process, the reamer 150 is then secured and the guide wire 142 is reversed in direction to disarticulate the guide wire 142 from the reamer 150. The reamer 150 is then removed from the body 102. Therefore, use of the reamer 150 as described, can serve to prepare the femoral head 124 and the acetabulum socket 128 for receiving or otherwise engaging each other or a prosthesis.

Figure 8:
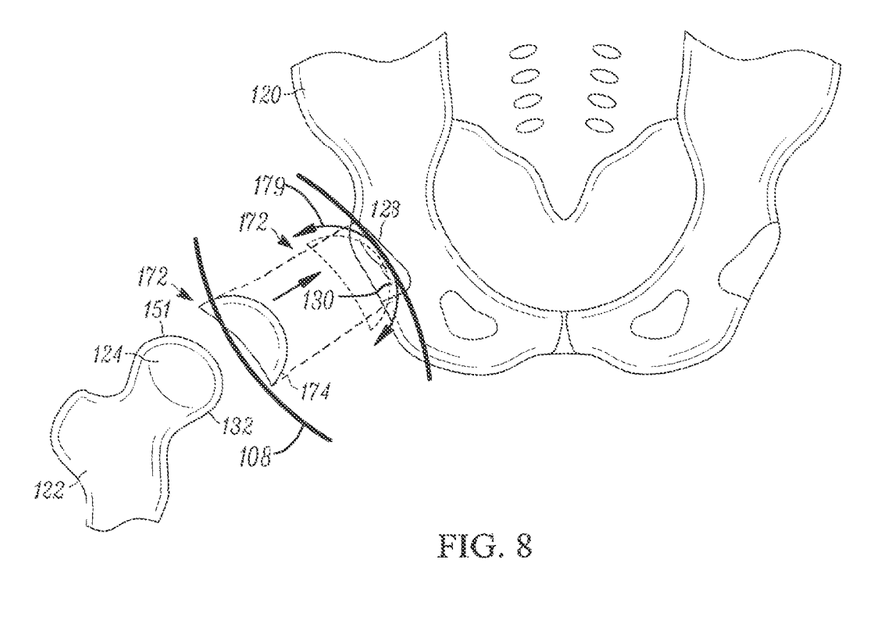
FIG. 8 illustrates the femur and pelvis of FIG. 3 and an example of a hemiarthroplasty cup prosthesis.
Figure 9:
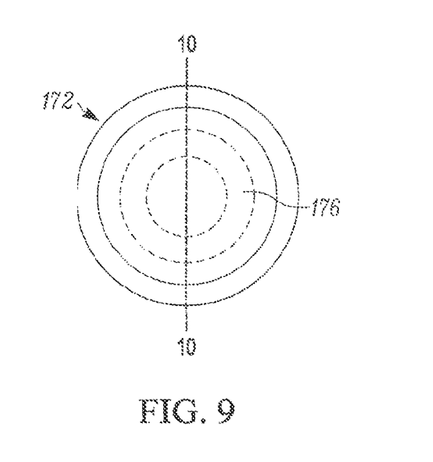
FIG. 9 illustrates a bottom view of the hemiarthroplasty cup prosthesis.
Figure 10:
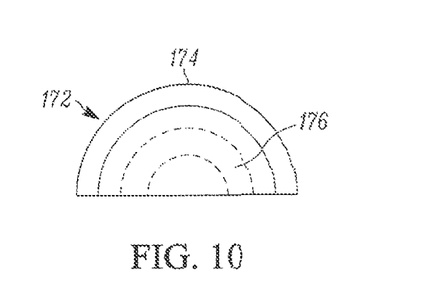
FIG. 10 illustrates a cross-sectional side view of the hemiarthroplasty cup prosthesis taken at line 10-10.

After completing the above procedure, various options exist for repairing or replacing the hip joint 104. Referring to FIG. 8, in at least one embodiment, where a hemiarthroplasty (half joint replacement) is desired, the guide wire 142 can be removed and a hemiarthroplasty cup 172 is inserted through the midanterior portal 108. The hemiarthroplasty cup 172, as seen in FIGS. 8, 9, and 10, is in at least some embodiments, a dual-sided hemispherical cup having a cup outer surface 174 and a cup inner surface 176. The hemiarthroplasty cup 172 can in at least some embodiments, be hemispherical, partially hemispherical, or substantially hemispherical, or otherwise sized to accommodate a reamed or unreamed joint bone. In addition, the hemiarthroplasty cup 172 can include alternate shapes, for example, an oblong/oval hemisphere. The cup outer surface 174 is shaped and sized to pivotably engage the acetabulum outer surface 130 and can be installed without the use of an assisting fixation method, such as cement, fasteners, bone growth agents, etc. Similarly, the cup inner surface 176 is shaped and sized to pivotably engage and articulate with the femoral head outer surface 132 (or another prosthesis installed thereon) and can be installed without the use of an assisting fixation method, such as cement, fasteners, bone growth agents, etc.

As the cup outer surface 174 can be installed without fixation, the femoral head 124 and the acetabulum socket 128 are allowed to articulate with the respective inner and outer cup surfaces 174, 176 of the hemiarthroplasty cup 172. Arrow 179 illustrates articulation of the hemiarthroplasty cup 172 between the femoral head 124 and the acetabulum socket 128. The need for assistive fixation methods are substantially reduced or eliminated due to, at least in part due to, the minimal violation of the hip joint area during installation. For example, the above procedure does not require cutting the entire ligamentous hip capsule (not shown) or significant cutting of the musculature of the hip, in order to prepare the hip joint 104 and install the hemiarthroplasty cup 172. The limited violation can maintain sufficient structure to support and secure the hemiarthroplasty cup 172 as needed. In at least some embodiments, the hemiarthroplasty cup 172 can be secured using assistive fixation methods, such as repair or reconstruction of the ligamentous capsule, or repair or reconstruction of the acetabular labrum, or another method as desired or necessary for one or more reasons.

Figure 11A:
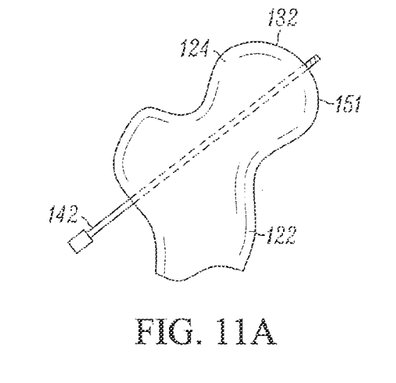
FIG. 11A illustrates the femur of FIG. 3 with the guide wire positioned therein.
Figure 11B:
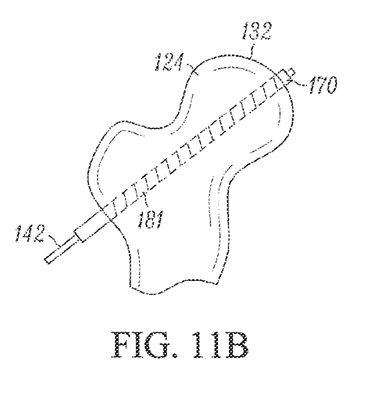
FIG. 11B illustrates the femur of FIG. 3 with an example of a cannulated drill positioned therein.
Figure 11C:
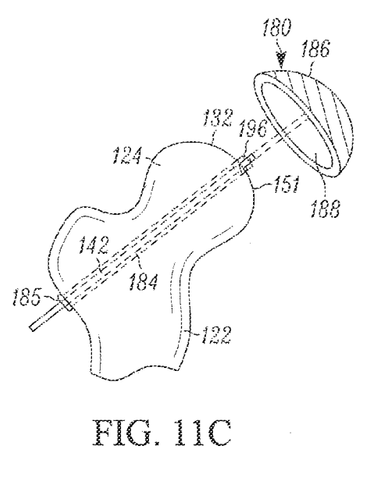
FIG. 11C illustrates the femur of FIG. 3 with an example of a cup femoral head prosthesis and an example of a cannulated fastener positioned therein.

As discussed above, various options exist for repairing or replacing the hip joint 104 after preparation of the hip joint 104. Referring now to FIGS. 11A-11E, in at least some embodiments, a cup femoral head prosthesis 180 can be installed on the femoral head 124. This procedure includes securing the cup femoral head prosthesis 180 to the femoral head 124. As seen in FIG. 11A, the guide wire 142 is positioned through the femur 122. In at least some embodiments, to fasten the cup femoral head prosthesis 180, a cannulated drill 181 is rotated over the guide wire 142, as seen in FIG. 11B, until it passes out of the femoral head outer surface 132 at the center 170 of the femoral head 124. The guide wire 142 is secured and the cup femoral head prosthesis 180 is brought into the hip joint 104 through the midanterior portal 108. The guide wire 142 is then articulated with the cup femoral head prosthesis 180, while a cannulated fastener, such as a cannulated screw 184 with an anchoring head 185, is inserted into the femur 122 over the guide wire 142, as seen in FIG. 11C. Further, as seen in FIG. 11C, the cup femoral head prosthesis 180 is illustrated. The cup femoral head prosthesis 180 can include numerous shapes, for example a shape similar to the hemiarthroplasty cup 172, such as a hemispherical, partially hemispherical, or substantially hemispherical cup shape. The cup femoral head prosthesis 180 includes a femoral cup outer surface 186 and a femoral cup inner surface 188.

The cup femoral head prosthesis 180 can be utilized with or without the hemiarthroplasty cup 172. As such, if a hemiarthroplasty cup 172 is not to be installed, the femoral cup outer surface 186 is shaped and sized to pivotably engage the acetabulum outer surface 130 (as seen in FIG. 8) after it has been reamed. If the hemiarthroplasty cup 172 is to be installed, the femoral cup outer surface 186 is shaped and sized to pivotably engage the cup inner surface 176 of the hemiarthroplasty cup 172. The femoral cup inner surface 188 is shaped and sized to fit the end 151 of the femoral head outer surface 132, after it has been reamed. The cup femoral head prosthesis 180 further includes a fastener receiving aperture 190 (see FIG. 11E) for engaging the cannulated screw 184. In at least some embodiments, the receiving aperture 190 extends there through and includes threads 194 for engaging a threaded end portion 196 of the cannulated screw 184.

Figure 11D:
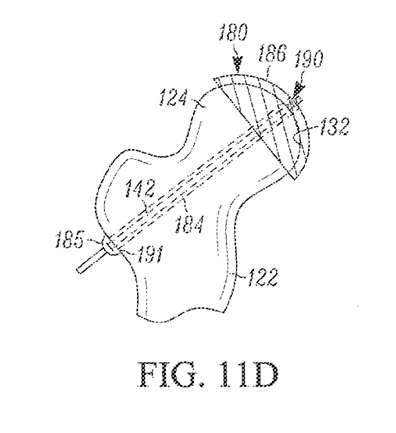
FIG. 11D illustrates the femur of FIG. 3 with the cup femoral head prosthesis secured to the femur.
Figure 11E:
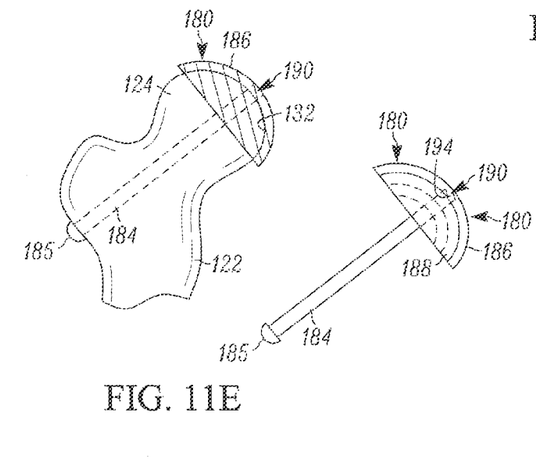
FIG. 11E illustrates the femur of FIG. 3 with a view of the cup femoral head prosthesis and cannulated fastener both inside and outside the hip joint.
Figure 12:
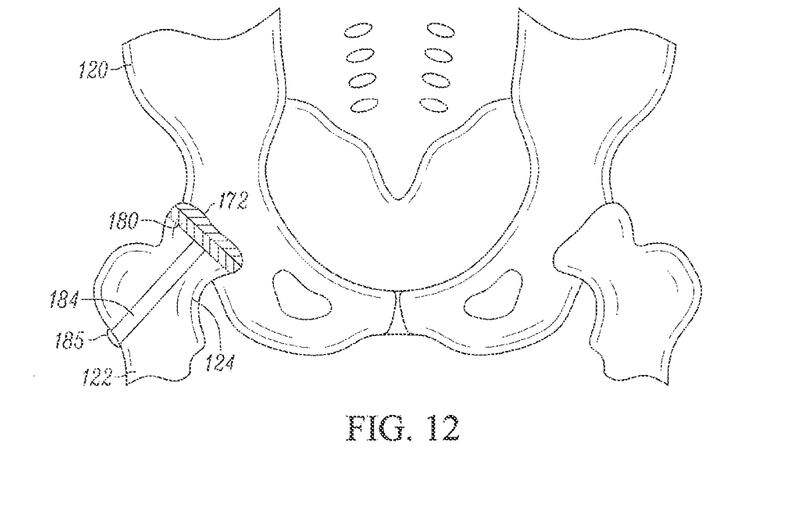
FIG. 12 illustrates a view of the hip joint of FIG. 2, post-installation of the cup femoral head prosthesis and the hemiarthroplasty cup prosthesis.

Referring to FIG. 11D, the cup femoral head prosthesis 180 is positioned over the femoral head outer surface 132 and the cannulated screw 184 is secured to the cup femoral head prosthesis 180. In at least some embodiments, this is accomplished by rotating the cannulated screw 184 to engage the threaded end portion 196 with the receiving aperture 190 and tightening of the cannulated screw 184 until the anchoring head 185 is secured against a lateral femoral cortex 191 of the femur 122, and the cup femoral head prosthesis 180 is secured onto the femur head outer surface 132. Once installed, the cup femoral head prosthesis 180 provides a smooth and secure pivoting surface. After the fastening has begun or has been completed, the guide wire 142 can be removed, as seen in FIG. 11E. In at least some embodiments, the installation of the cup femoral head prosthesis 180 is followed by the insertion of the hemiarthroplasty cup 172 into the hip joint 104, where the hemiarthroplasty cup 172 can be brought into the hip joint 104 through the midanterior portal 108. Upon completion of the installation of the prosthesis, the traction is taken off the hip joint 104 and the femoral head prosthesis 180 is brought to articulate with the hemiarthroplasty cup 172, as seen in FIG. 12.

The cup femoral head prosthesis 180 and the hemiarthroplasty cup 172 can be utilized together, or in isolation as a hemiarthroplasty. In addition, the cup femoral head prosthesis 180 and the hemiarthroplasty cup 172 can be utilized together, or in isolation, without performing a reaming procedure on a joint. The cup femoral head prosthesis 180 is comprised of materials suitable for insertion into the body 102, such as cobalt chrome, steel, aluminum, and/or other alloys, metals, ceramics, polymer composites, etc. The inner surface 188 of the cup femoral head prosthesis 180 can be comprised of a porous, grit blasted, or otherwise oriented surface amenable to either ongrowth or ingrowth of the bone from the femoral head outer surface 132. In addition, the hemiarthroplasty cup 172 is comprised of materials suitable for insertion into the body 102, such as polyethylene, cobalt chrome, steel, aluminum, and/or other alloys, metals, ceramics, or polymer composites. The aforementioned material lists are not exclusive and therefore, other materials not listed or currently unknown can be used if suitable for such a purpose. Although the aforementioned procedure is described in relation to hip joint 104, the components and procedures can be modified to accommodate repair and/or replacement of various other joints in the human body, such as a shoulder joint. For example, the shape of the reamer 150 could be modified to ream other ball and socket joints. Further, the components and procedures can be modified to accommodate repair and/or replacement of a hip joint or other joints in the body of an animal as well.

It is specifically intended that the method and device for joint replacement not be limited to the embodiments and illustrations contained herein, but include modified forms of those embodiments including portions of the embodiments and combinations of elements of different embodiments as come within the scope of the following claims. Further, the steps outlined above can be modified in various manners, such as performance in one or more alternate orders. The addition or exclusion of any step(s) discussed or not discussed, does not preclude a desired completion of the procedure.

I claim:

1. A method of joint replacement comprising:
   forming one or more portals adjacent a hip joint that includes, a femur with a femoral head and a pelvis with an acetabulum socket; and
   inserting a hemiarthroplasty cup through one of the one or more portals, the hemiarthroplasty cup having a cup inner surface and a cup outer surface, between a femoral head outer surface of the femoral head and an acetabulum outer surface of the acetabulum socket so that the hemiarthroplasty cup can freely articulate against both the femoral head outer surface and the acetabulum outer surface, wherein at least one of the femoral head outer surface and the acetabulum outer surface are unreamed;
   wherein the hemiarthroplasty cup has a hemispherical shape.

2. The method of claim 1, wherein both the femoral head outer surface and acetabulum outer surface are unreamed and uncut, and wherein the cup inner surface engages the femoral head outer surface and the cup outer surface engages the acetabulum outer surface.

3. The method of claim 1, further including inserting a guide wire through a portion of the femur to extend out of the femoral head.

4. The method of claim 3, further including securing a reamer blade to the guide wire.

5. The method of claim 4, further including reaming the femoral head outer surface to at least one of access cancellous bone and remove damaged cartilage.

6. The method of claim 5, further including unsecuring the reamer blade from the guide wire.

7. The method of claim 4, further including reaming the acetabulum outer surface to at least one of access cancellous bone and remove damaged cartilage.

8. The method of claim 7, further including unsecuring the reamer blade from the guide wire.

9. The method of claim 1, wherein the hemiarthroplasty cup is installed between the femoral head outer surface of the femoral head and the acetabulum outer surface of the acetabulum socket without assisting fixation.

10. The method of claim 9, further comprising inserting a cup femoral head prosthesis adjacent to the femoral head outer surface and the hemiarthroplasty cup, wherein the hemiarthroplasty cup is comprised of a polymer and the cup femoral head prosthesis is comprised of a metal alloy.

11. A method of joint replacement comprising:
forming one or more portals adjacent a hip joint that includes, a femur with a femoral head and a pelvis with an acetabulum socket; and
inserting a hemiarthroplasty cup through one of the one or more portals, the hemiarthroplasty cup having a cup inner surface and a cup outer surface, between a femoral head outer surface of the femoral head and an acetabulum outer surface of the acetabulum socket, wherein both the femoral head outer surface and the acetabulum outer surface are unaltered;
wherein the cup inner surface engages the femoral head outer surface and the cup outer surface engages the acetabulum outer surface so that the hemiarthroplasty cup can freely articulate against both the femoral head outer surface and the acetabulum outer surface.

12. The method of claim 11, wherein the hemiarthroplasty cup is installed between the femoral head outer surface of the femoral head and the acetabulum outer surface of the acetabulum socket without assisting fixation.

13. The method of claim 12, wherein the hemiarthroplasty cup is installed without cutting completely through a ligamentous hip capsule or musculature of the hip joint.

* * * * *